United States Patent [19]

Miyazaki et al.

[11] Patent Number: 4,507,494

[45] Date of Patent: Mar. 26, 1985

[54] PROCESS FOR THE PRODUCTION OF A DIESTER OF OXALIC ACID

[75] Inventors: Haruhiko Miyazaki; Yasushi Shiomi, both of Ube; Satoru Fujitus, Yamaguchi; Katsuro Masunaga; Hiroshi Yanagisawa, both of Ube, all of Japan

[73] Assignee: Ube Industries, Ltd., Yamaguchi, Japan

[21] Appl. No.: 460,574

[22] Filed: Jan. 24, 1983

[30] Foreign Application Priority Data

Jan. 26, 1982 [JP] Japan ................................. 57-9517

[51] Int. Cl.$^3$ .............................................. C07C 67/36
[52] U.S. Cl. ..................................... 560/193; 502/74; 502/102; 502/171; 502/178; 502/182; 502/185; 502/213; 502/217; 502/227; 502/230; 502/242; 560/190; 560/204
[58] Field of Search ...................... 560/204, 190, 193; 502/74, 102, 171, 178, 182, 185, 213, 217, 227, 230, 242

[56] References Cited

U.S. PATENT DOCUMENTS 4,229,589 10/1980 Nishimura et al. ................. 560/204
4,229,591 10/1980 Nishimura et al. ................. 560/204

FOREIGN PATENT DOCUMENTS 51-29428 3/1976 Japan .

Primary Examiner—Natalie Trousof
Assistant Examiner—Vera C. Clarke
Attorney, Agent, or Firm—Sherman & Shalloway

[57] ABSTRACT

In a process for preparing a diester of oxalic acid by the vapor phase catalytic reaction of carbon monoxide with an ester of nitrous acid in the presence of a catalyst composed of a solid carrier and a catalyst component supported on the carrier, the improvement wherein said catalyst component is composed of (a) a platinum-group metal or a salt thereof, and
(b) at least one member selected from the group consisting of Ti and an oxide thereof.

9 Claims, No Drawings

PROCESS FOR THE PRODUCTION OF A DIESTER OF OXALIC ACID

This invention relates to an improved process for preparing a diester of oxalic acid by the vapor (or gaseous) phase catalytic reaction of carbon monoxide with an ester of nitrous acid in the presence of a catalyst composed of a solid carrier and a catalyst component supported on the carrier. According to this process, the diester of oxalic acid can be produced at a higher selectivity with a longer catalyst life than a conventional process involving using a platinum-group metal or a salt thereof alone as the catalyst component while maintaining an excellent space time yield.

More specifically, this invention relates, in the aforesaid vapor phase catalytic reaction, to the improvement which comprises using a catalyst composed of a solid carrier and a catalyst component supported on the carrier, said component being composed of (a) a platinum-group metal or a salt thereof and (b) at least one member selected from the group consisting of Ti and an oxide thereof.

The process for preparing a diester of oxalic acid by the vapor phase catalytic reaction of carbon monoxide with an ester of nitrous acid in the presence of a catalyst composed of a solid carrier and metallic palladium or a salt thereof supported on the carrier is known (U.S. Pat. No. 4,229,591). This U.S. Patent, however, does not at all refer to the use of a co-catalyst component or a catalyst having such a second catalyst component supported together.

Japanese Laid-Open Patent Publication No. 22666/1980 (published on Feb. 18, 1980; corresponding UK Patent Application 2025950A) discloses another process for the production of a diester of oxalic acid by a similar vapor phase catalytic reaction to that shown in the above U.S. Patent. The Japenese patent document exemplifies palladium, rhodium, iridium, platinum, gold and salts of these metals as ingredients of the catalyst, and iron, copper and salts of these as a carrier which concurrently serves as a catalyst promoter.

To the best of the knowledge of the present inventors, the prior literature including the two references cited above does not disclose the use of Ti or an oxide thereof as a catalyst component or catalyst promotor component for use in the vapor phase catalytic reaction of carbon monoxide with an ester of nitrous acid.

The present inventors have worked on the improvement of catalysts used in the aforesaid vapor phase catalytic reaction, and consequently found that by using a catalyst component supported on a solid carrier and composed of the aforesaid components (a) and (b), a diester of oxalic acid can be produced at a higher selectivity with a longer catalyst life than in the case of using a conventional catalyst comprising the component (a) on a solid carrier but not containing the component (b), while maintaining an excellent space time yield.

The work of the present inventors has shown that the use of the aforesaid catalyst composed of the components (a) and (b) supported concurrently on a solid carrier is advantageous over the conventional catalyst not containing the component (b) in that (i) the diester of oxalic acid can be produced at a higher selectivity while the space time yield of the oxalate in the initial stage of the reaction remains almost unchanged, and (ii) in a long-term reaction, the decrease in the selectivity and the space time yield of the oxalate is very small, and the oxalate can be produced stably over a long period of time.

It has also been found that the aforesaid catalyst is preferably formed by impregnating a solid carrier with an aqueous solution of a water-soluble salt of a platinum-group metal and an aqueous solution of a water-soluble salt of Ti, treating the impregnated solid carrier with an alkali, and then treating the alkali-treated product with a reducing agent in the liquid or gaseous phase; and that alternatively, the above procedure may be carried out by first impregnating the solid carrier with the aqueous solution of a water-soluble salt of a platinum-group metal, treating the impregnated solid carrier with an alkali, dipping the alkali-treated product in the aqueous solution of a water-soluble salt of Ti, and then treating the resulting product with a reducing agent in the liquid or gaseous phase.

It is an object of this invention therefore to provide an improved process for producing a diester of oxalic acid by vapor-phase catalytic reaction using a specified catalyst.

The above and other objects of this invention along with its advantages will become more apparent from the following description.

Examples of the platinum-group metal used as the catalyst component (a) in this invention are palladium, platinum, rhodium, ruthenium and iridium. They may be used as a mixture of two or more. Palladium, either alone or in combination with another platinum-group metal, is preferred. Examples of the salt of the platinum-group metal include nitrates, sulfates, phosphates, halides, acetates, oxalates and benzoates of the above-exemplified metals.

Ti or an oxide thereof can be used as the catalyst component (b) in this invention. In some cases, the component (b) may be in the form of a salt of Ti such as its nitrate, halide or sulfate.

The ratio of the component (a) to the component (b) may be properly selected. Preferably, the atomic ratio of the component (a) to the component (b), as metal, is from 10,000:1 to 1:5, preferably from 5,000:1 to 1:2. If the amount of the component (b) is too small as compared with the compound (a), the effect of prolonging the life of the catalyst is reduced. If it is too large, the space time yield and selectivity of the diester of oxalic acid is decreased. Accordingly, the ratio within the above-exemplified range is advantageously used.

The amount of the component (a) supported on the solid carrier is preferably 0.01 to 10% by weight, more preferably 0.1 to 2% by weight, as metal based on the weight of the solid carrier.

In this invention, both the components (a) and (b) are supported on the solid carrier. Examples of the carrier used include activated carbon, alumina (such as α-alumina or γ-alumina), silica, diatomaceous earth, silicon carbide, pumice, zeolite and molecular sieves. Among these, α-alumina, γ-alumina, silica, and silicon carbide are especially preferred.

There is no restriction on the manner of supporting the catalytic metal components on the solid carrier, and any known means of supporting can be used. Preferably, however, the catalyst is prepared by impregnating a solid carrier with an aqueous solution of a water-soluble salt of a platinum-group metal and an aqueous solution of a water-soluble salt of Ti, treating the impregnated solid carrier with an alkali, and then treating the alkali-treated product with a reducing agent in the liquid or gaseous phase. Alternatively, the above procedure may be carried out by first impregnating the solid carrier with the aqueous solution of a water-soluble salt of a platinum-group metal, treating the impregnated solid carrier with an alkali, dipping the alkali-treated product in the aqueous solution of a water-soluble salt of Ti, and then treating the resulting product with a reducing agent in the liquid or gaseous phase.

Examples of the water-soluble salt of the platinum-group metal are nitrates, sulfates, acetates, phosphates, chlorides, chloro complex salts, and amine complex salts of the above-exemplified platinum-group metals. Examples of the water-soluble salt of Ti are the nitrate, sulfate, acetate, phosphate and chloride.

The impregnation may be effected by dipping the solid carrier in an aqueous solution containing the water-soluble salt of the platinum-group metal and the water-soluble salt of Ti, or by dipping the solid carrier in a desired sequence in aqueous solutions of the respective water-soluble salts. As stated above, it is also possible to dip the solid carrier in the aqueous solution containing the water-soluble salt of the platinum-group metal, treat the impregnated solid carrier with an alkali, and then to dip the impregnated carrier in the aqueous solution of the water-soluble salt of Ti. The dipping may be performed at a temperature of, for example, about 0° C. to about 90° C. and a period of, for example, about 0.1 to about 10 hours. If desired, the impregnation may also be carried out by spraying the aforesaid aqueous solution onto the solid carrier.

Preferably, the above aqueous solutions are solutions prepared by dissolving the above water-soluble salts in an acidic aqueous solution containing about 0.01 to about 10% by weight of an acidic compound. The use of the acidic aqueous solution serves to aid in the dissolving of the salt of the platinum-group metal and the salt of Ti and to prevent the formation and precipitation of a hydroxide and oxide of the platinum-group metal and Ti by hydrolysis. Specific examples of the acidic compound include mineral acids such as hydrochloric acid, nitric acid, sulfuric acid and phosphoric acid and organic acids such as acetic acid. These acidic compounds may, if desired, be used as a mixture of two or more.

The carrier impregnated with the aqueous solutions containing the water-soluble salts is then separated, and if desired washed with water and then dried by, for example, air drying, vacuum drying or heat drying, after which it is subjected to the alkali treatment.

The alkali treatment can be effected by adding the carrier impregnated with the aqueous solutions of the above water-soluble salts to an alkaline aqueous solution containing, for example, about 0.05 to about 10% by weight of an alkaline compound, and stirring the mixture at a temperature of, for example, about 10° to about 90° C. for a period of, for example, about 0.5 to about 10 hours. Examples of the alkaline compound include the hydroxides and salts of alkali metals or alkaline earth metals, for example sodium hydroxide, potassium hydroxide, calcium hydroxide, barium hydroxide, sodium carbonate, sodium hydrogen carbonate and potassium carbonate. If desired, these alkaline compounds may be used as a mixture of two or more. There is no special limitation on the amount of the alkaline compound used. Preferably, it is about 2 to about 40 moles per mole of the sum of the platinum-group metal salt and the Ti salt.

After the alkali treatment, the product is optionally washed with water, etc. and dried. The product is then treated with a reducing agent in the liquid or gaseous phase to form the final catalyst.

The liquid-phase reduction is carried out by using such reducing agents as hydrazine, formaldehyde, sodium formate and formic acid. Specifically, it can be carried out by adding the alkali-treated product to an aqueous solution of the reducing agent in a concentration of about 1 to about 10% by weight, and stirring the mixture at a temperature of, say, about 10° to about 50° C. for a period of, say, about 0.5 to about 10 hours.

The alkaline-treated product may be added directly to the aqueous solution of the reducing agent in performing the reduction. It is more effective, however, to separate the alkali-treated solid product by a solid-liquid separating procedure such as filtration or decantation, wash and dry it, then add the dried product to the aqueous solution of the reducing agent, and subject the dried product to the reducing treatment in the liquid phase.

Examples of reducing agents suitable for use in the gaseous phase reduction are hydrogen, carbon monoxide and ammonia. These reducing agents may be used after being diluted with inert gases such as nitrogen or carbon dioxide. The gaseous phase reduction can be carried out by passing the gaseous reducing agent through the alkali-treated product at a temperature of, for example, about 50° to about 800° C. for a period of, say, about 1 to about 10 hours.

The starting gases used in this invention in the reaction of synthesizing the diester of oxalic acid are carbon monoxide and a nitrous acid ester, and sometimes, contain alcohol, nitrogen oxides, etc. as will be stated hereinbelow. In any case, the starting gases contain carbon monoxide effective for the aforesaid vapor phase reducing treatment. Accordingly, as one means of subjecting the aforesaid alkali-treated product to a vapor-phase reducing treatment, there may also be employed a method which comprises feeding the alkali-treated product into an apparatus for the synthesis of the diester of oxalic acid, and prior to the reaction of synthesizing the diester of oxalic acid, subjecting it to a vapor-phase reducing treatment by using a gaseous mixture of carbon monoxide and a nitrous acid ester which may optionally contain alcohol, nitrogen oxides, etc.

According to the process of this invention, carbon monoxide is reacted with an ester of nitrous acid in the vapor phase in the presence of the catalyst prepared as above which is composed of a solid carrier and a catalyst component supported on it, said component being composed of (a) a platinum-group metal or a salt thereof and (b) at least one member selected from Ti and an oxide thereof. This reaction can be schematically shown by the following equation.

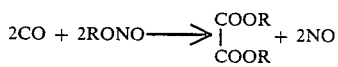

(R = alkyl or cycloalkyl)

As the above scheme shows, this reaction yields nitrogen monoxide equivalent to the consumed nitrous acid ester. Accordingly, the nitrogen monoxide thus formed may be recycled as the starting material for the above reaction by introducing an alcohol and a gas containing molecular oxygen to react them with the nitrogen monoxide as schematically shown below and recovering the resulting nitrous acid ester.

$$2NO + \tfrac{1}{2}O_2 + 2ROH \longrightarrow 2RONO + H_2O$$

(R = alkyl or cycloalkyl)

An ester of nitrous acid with a saturated monohydric aliphatic alcohol having 1 to 8 carbon atoms or an alicyclic alcohol having 1 to 8 carbon atoms is preferred as the ester of nitrous acid. Examples of the aliphatic alcohol are methanol, ethanol, n-propanol, isopropanol, n-butanol, isobutanol, sec-butanol, tert-butanol, n-amyl alcohol, isoamyl alcohol, hexanol and octanol, and examples of the alicyclic alcohol include cyclohexanol and methyl-cyclohexanol. These alcohols may contain a substituent, such as an alkoxy group, which does not inhibit the reaction.

The concentration of the ester of nitrous acid used may be varied over a wide range. To obtain a satisfactory rate of reaction, it is desirable to adjust the concentration of the nitrous acid ester in the starting gaseous mixture introduced into the reactor at 1% by volume or higher, for example about 5 to about 30% by volume.

Carbon monoxide used in the process of this invention may be pure or may be diluted with an inert gas such as nitrogen. The concentration of carbon monoxide in the reaction zone may be varied over a wide range and is, for example, in the range of 10 to 90% by volume.

The reaction is carried out under such conditions that no liquid phase is formed in the reaction zone (namely, in the gaseous or vapor phase). These conditions may vary depending upon the reaction temperature, the reaction pressure, the type and concentration of the nitrous acid ester, etc. Thus, these conditions may be properly selected so that the reaction is carried out in the vapor phase.

The reaction proceeds rapidly even at low temperatures, and side-reactions occur less as the reaction temperature is lower. It is desirable therefore to perform the reaction at relatively low temperature at which the desired space time yield can be maintained, for example at a temperature of about 50° C. to about 200° C., preferably at about 80° C. to about 150° C. The reaction pressure can also be selected properly. For example, it is atmospheric pressure to about 10 kg/cm$^2$.G, preferably atmospheric pressure to about 5 kg/cm$^2$.G. Pressures below the above-specified lower limit, for example reduced pressures of down to about 200 mmHg, can also be used.

The catalytic reaction in accordance with this invention may be carried out in a fixed or fluidized bed. The time of contact between the starting gaseous mixture and the catalyst can be properly chosen. For example, the contact time is not more than about 20 seconds, preferably about 0.2 to about 10 seconds.

The nitrous acid ester can be prepared, for example, by reacting an alcohol with a nitrogen oxide in the optional presence of molecular oxygen. The reaction product gas contains the unreacted alcohol and nitrogen oxide (particularly nitrogen monoxide) and at times, traces of water and oxygen in addition to the nitrous acid ester. In the process of this invention, this product gas containing the nitrous acid ester can be used as the starting nitrous acid ester, and good results can be obtained even when such a nitrite containing impurities is used.

The following examples illustrate the practice of the process of the invention in greater detail.

CATALYST PREPARATION EXAMPLE

Palladium chloride (1.46 parts by weight) and 0.16 part by weight of titanium chloride were dissolved in 68.4 parts by weight of a 0.9% by weight aqueous solution of hydrochloric acid, and 50 parts by weight of spherical α-alumina particles having a diameter of 3 mm were dipped in the solution. The solution was stirred at room temperature for about 2 hours.

The alumina impregnated with palladium chloride and titanium chloride was collected by decantation, dried, and then dipped in a solution of 1.5 parts by weight of sodium hydroxide in 68.5 parts by weight of water. The solution was stirred at about 60° C. for about 4 hours to perform alkali treatment.

Then, the alkali-treated product was washed with water until the washings became neutral and a chlorine ion was no longer detected. Then, it was dried, and subjected to a reducing treatment in a stream of hydrogen at 500° C. for 3 hours to give a spherical solid catalyst having a particle diameter of 3 mm and composed of α-alumina and palladium and titanium deposited thereon.

EXAMPLE 1

A glass reaction tube having an inside diameter of 20 mm and a length of 55 cm was filled with 2 ml of a catalyst prepared in accordance with Catalyst Preparation Example and composed of spherical α-alumina particles with a diameter of 3 mm and 0.4% by weight of palladium and 0.023% by weight (calculated as metals) deposited thereon. Glass beads were further filled in the reaction tube and placed on the catalyst layer to a height of 24 cm.

The reaction tube was fixed vertically, and an annular electric heater was mounted on the outside of the reaction tube to maintain the temperature of the catalyst layer at 110° C.

From the top of the reaction tube, a gaseous mixture consisting of 20% by volume of carbon monoxide, 15% by volume of methyl nitrite, 15% by volume of methanol, 3% by volume of nitrogen monoxide and 47% by volume of nitrogen was fed into the reactor at a rate of 20 liters/hr (S.T.P.).

The reaction product which left the reaction tube was passed through methanol to collect dimethyl oxalate. Low-boiling compounds not collected by methanol were then condensed by cooling with dry ice/methanol and collected. The liquids collected 8 hours after the initiation of the reaction and after the periods of time elapsed which are indicated in Table 1 were analyzed by gas chromatography, and the space time yield (g/liter-hr) of dimethyl oxalate was measured.

EXAMPLES 2 AND 3

The procedure of Example 1 was followed except that the reaction temperature was changed to 130° C. (Example 2) and 150° C. (Example 3).

EXAMPLE 4

The procedure of Example 1 was followed except that there was used 2 ml of a catalyst composed of spherical α-alumina particles with a particle diameter of 3 mm and 0.5% by weight of palladium and 2 ppm of titanium (calculated as metals) deposited thereon and prepared in accordance with Catalyst Preparation Example.

EXAMPLES 5 AND 6

The procedure of Example 4 was followed except that the reaction temperature was changed to 130° C. (Example 5), and 150° C. (Example 6).

EXAMPLE 7

The procedure of Example 1 was followed except that there was used 2 ml of a catalyst prepared in accordance with Catalyst Preparation Example and composed of spherical α-alumina particles with a particle diameter of 3 mm and 0.5% by weight of palladium and 0.23% by weight of titanium (calculated as metals).

EXAMPLE 8

The procedure of Example 7 was followed except that the reaction temperature was changed to 130° C.

COMPARATIVE EXAMPLE 1

A catalyst composed of spherical α-alumina particles with a particle diameter of 3 mm and 0.5% by weight of palladium deposited thereon was prepared in the same way as in Catalyst Preparation Example except that titanium chloride was not added. The same reaction as in Example 1 was carried out except that 2 ml of the resulting catalyst was used.

COMPARATIVE EXAMPLE 2

A catalyst composed of spherical α-alumina particles with a particle diameter of 3 mm and 0.55% by weight of palladium deposited thereon was prepared in the same way as in Catalyst Preparation Example except that titanium chloride was not added. The same reaction as in Example 1 was carried out except that 2 ml of the resulting catalyst was used, and the reaction temperature was changed to 130° C.

COMPARATIVE EXAMPLE 3

The procedure of Comparative Example 2 was followed except that the reaction temperature was changed to 150° C.

Table 1 summarizes the results obtained in Examples 1 to 8 and Comparative Examples 1 to 3.

In Table 1, the space time yield ratio of dimethyl oxalate is the ratio of the space time yield at each elapsed time to that at 8 hours after the initiation of the reaction, the latter being taken as 100 g/liter-hour, and calculated in accordance with the following equation.

$$\text{Ratio of the space time yield of dimethyl oxalate} = \frac{\text{Space time yield of dimethyl oxalate at each reaction time elapsed}}{\text{Space time yield of dimethyl oxalate at 8 hours after the start of the reaction}} \times 100$$

TABLE 1

| | | Catalyst | | | Reaction | Ratio of the space | Selectivity based on CO (%) | | |
| | | Pd (wt. %) | Ti (ppm) | Ti/Pd (atomic-ratio) | Reaction temperature (°C.) | time elapsed (hr) | time yield of dimethyl oxalate | Dimethyl oxalate | Dimethyl carbonate | $CO_2$ |
|---|---|---|---|---|---|---|---|---|---|---|
| Example | 1 | 0.4 | 223 | 0.1 | 110 | 199 | 104 | 99.1 | 0.9 | ~0 |
| | | | | | | 600 | 91 | 99.1 | 0.9 | ~0 |
| | 2 | " | " | " | 130 | 270 | 96 | 97.6 | 2.2 | 0.2 |
| | | | | | | 600 | 92 | 97.8 | 2.1 | 0.1 |
| | 3 | " | " | " | 150 | 294 | 101 | 95.4 | 4.4 | 0.2 |
| | | | | | | 600 | 82 | 94.1 | 5.7 | 0.2 |
| | 4 | 0.5 | 2 | 0.001 | 110 | 222 | 94 | 98.4 | 1.0 | 0.6 |
| | | | | | | 558 | 80 | 98.2 | 1.1 | 0.7 |
| | 5 | " | " | " | 130 | 294 | 97 | 97.0 | 2.2 | 0.8 |
| | | | | | | 600 | 94 | 96.8 | 2.4 | 0.8 |
| | 6 | " | " | " | 150 | 198 | 96 | 94.4 | 4.8 | 0.8 |
| | 7 | " | 2250 | 1 | 110 | 294 | 89 | 98.1 | 1.5 | 0.4 |
| | | | | | | 600 | 84 | 98.2 | 1.5 | 0.3 |
| | 8 | " | " | " | 130 | 294 | 94 | 96.0 | 3.5 | 0.5 |
| | | | | | | 600 | 86 | 96.4 | 3.1 | 0.5 |
| Comparative Example | 1 | " | 0 | 0 | 110 | 342 | 83 | 98.9 | 1.1 | ~0 |
| | | | | | | 670 | 63 | 99.1 | 0.9 | ~0 |
| | 2 | 0.55 | " | " | 130 | 199 | 67 | 98.1 | 1.5 | 0.6 |
| | | | | | | 367 | 37 | 97.6 | 1.6 | 0.6 |
| | 3 | " | " | " | 150 | 264 | 88 | 96.2 | 3.3 | 0.5 |
| | | | | | | 575 | 72 | 96.3 | 3.2 | 0.5 |

EXAMPLE 9

A jacketed reaction tube having an inside diameter of 28.4 mm was filled with 1,870 g of a catalyst composed of spherical α-alumina particles with a particle diameter of 3 mm and 0.5% by weight of palladium and 0.023% by weight of titanium (calculated as metals)[Ti/Pd atomic ratio=0.1] and prepared in accordance with Catalyst Preparation Example. The catalyst layer was divided into a top portion, a middle portion and a bottom portion, and the temperatures of these portions were independently controlled. A starting gaseous mixture composed of 10% by volume of methyl nitrite, 20% by volume of carbon monoxide, 3% by volume of nitrogen monoxide, 4% by volume of methanol and 63% by volume of nitrogen was passed through the catalyst layer at a space velocity (S.T.P.) for 3,000 $hr^{-1}$, and reacted continuously for 950 hours at a reaction temperature of 115° to 120° C. and a reaction pressure of 2.5 $kg/cm^2G$. Over the 950-hour period, the space time yield and selectively of dimethyl oxalate and the temperature of the catalyst layer remained nearly constant. This led to the determination that the activity of the catalyst was very stable.

The results are shown in Table 2.

TABLE 2

| Operating time (hr) | Temperature for preheating the starting gas (°C.) | Temperature of the catalyst layer (°C.) | | | Space time yield of dimethyl oxalate (g/l-hr) | Selectivity (%) based on CO* | | |
|---|---|---|---|---|---|---|---|---|
| | | Top (inlet) | Middle (center) | Bottom (outlet) | | Dimethyl oxalate | Dimethyl carbonate | $CO_2$ |
| 100 | 108 | 113 | 120 | 116 | 429 | — | — | — |
| 300 | 108 | 117 | 119 | 117 | 436 | 97.8 | 1.49 | 0.74 |
| 700 | 112 | 117 | 120 | 119 | 453 | — | — | — |
| 900 | 108 | 115 | 120 | 120 | 462 | 98.7 | 0.84 | 0.44 |

*The mark "—" indicate that no measurement was made.

EXAMPLE 10

The procedure of Example 1 was followed except that a gaseous mixture composed of 5% by volume of ethyl nitrite, 20% by volume of carbon monoxide and 75% by volume of $N_2$ at the inlet of the reactor was used, and the space velocity of the gaseous mixture was changed to 5,000 $hr^{-1}$. In the initial stage of the reaction, the space time yield of diethyl oxalate was 490 g/liter-hour, and the change of the ratio of the space time yield of diethyl oxalate with the elapsed reaction time was nearly the same as that in Example 1. In the initial stage of the reaction, the selectivity based on CO was 97.4% for diethyl oxalate and 2.0% for diethyl carbonate, and the amount of by-product $CO_2$ was small.

What we claim is:

1. In a process for preparing a diester of oxalic acid by the vapor phase catalytic reaction of carbon monoxide with an ester of nitrous acid in the presence of a catalyst composed of a solid carrier and a catalyst component supported on the carrier, the improvement wherein said catalyst component is composed of
    (a) a platinum-group metal or a salt thereof, and
    (b) at least one member selected from the group consisting of Ti and an oxide thereof.

2. The process of claim 1 wherein said ester of nitrous acid is an ester of nitrous acid with an alcohol having 1 to 8 carbon atoms selected from the group consisting of saturated monohydric aliphatic alcohols and alicyclic alcohols.

3. The process of claim 1 wherein the catalytic reaction is carried out at a temperature of about 50° C. to about 200° C.

4. The process of claim 1 wherein the catalytic reaction is carried out at a pressure ranging from atmospheric pressure to about 10 $kg/cm^2G$.

5. The process of claim 1 wherein the atomic ratio of the component (a) to the component (b) as metal is from 10,000:1 to 1:5.

6. The process of claim 1 wherein the amount of the component (a) supported is about 0.01 to about 10% by weight calculated as the platinum-group metal based on the weight of the carrier.

7. The process of claim 1 wherein said catalyst is prepared by impregnating the solid carrier with an aqueous solution of a water-soluble salt of the platinum-group metal and an aqueous solution of a water-soluble salt of Ti, treating the impregnated solid carrier with an alkali, and then subjecting the alkali-treated product to reducing treatment in the liquid or gaseous phase.

8. The process of claim 1 wherein said catalyst is prepared by impregnating the solid carrier with an aqueous solution of a water-soluble salt of the platinum-group metal, treating the impregnated solid carrier with an alkali, dipping the alkali-treated product in an aqueous solution of a water-soluble salt of Ti, and then subjecting the resulting product to reducing treatment in the liquid or gaseous phase.

9. The process of claim 7 or 8 wherein said alkali is selected from the group consisting of hydroxides, carbonates and bicarbonates of alkali metals or alkaline earth metals.

* * * * *